United States Patent
Balagurusamy et al.

(10) Patent No.: US 10,533,984 B2
(45) Date of Patent: Jan. 14, 2020

(54) DISTINGUISHING FLUIDS BASED UPON DETERMINATION AND ANALYSIS OF DIGITAL IMAGE COLOR SPACE CHARACTERISTICS

(71) Applicant: International Business Machines Corporation, Armonk, NY (US)

(72) Inventors: Venkat K. Balagurusamy, Suffern, NY (US); Donna N Eng Dillenberger, Yorktown Heights, NY (US); Joseph Ligman, Wilton, CT (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 128 days.

(21) Appl. No.: 15/831,513

(22) Filed: Dec. 5, 2017

(65) Prior Publication Data

US 2019/0170724 A1    Jun. 6, 2019

(51) Int. Cl.
| | |
|---|---|
| G06T 7/20 | (2017.01) |
| G01N 33/28 | (2006.01) |
| G06T 7/00 | (2017.01) |
| G01N 11/00 | (2006.01) |
| G01N 21/17 | (2006.01) |

(52) U.S. Cl.
CPC .......... *G01N 33/28* (2013.01); *G06T 7/0004* (2013.01); *G06T 7/20* (2013.01); *G01N 2011/008* (2013.01); *G01N 2021/1765* (2013.01); *G01N 2291/028* (2013.01)

(58) Field of Classification Search
None
See application file for complete search history.

(56) References Cited

U.S. PATENT DOCUMENTS

| | | | |
|---|---|---|---|
| 7,166,828 | B2 | 1/2007 | Yamaguchi et al. |
| 8,528,589 | B2 | 9/2013 | Miller et al. |
| 8,675,118 | B2 | 3/2014 | Ryu |
| 9,599,553 | B2 | 3/2017 | Pollmann |
| 9,743,020 | B2 | 8/2017 | Zheng et al. |
| 2016/0305864 | A1 | 10/2016 | Vanapalli et al. |
| 2017/0038295 | A1 | 2/2017 | Aizenberg et al. |
| 2017/0234804 | A1 | 8/2017 | Vander Neut et al. |

(Continued)

OTHER PUBLICATIONS

Sabouri, A., Yetisen, A. K., Sadigzade, R. et al. (2017). Three-dimensional microstructured lattices for oil sensing. Energy & Fuels, 31(3), pp. 2524-2529.

(Continued)

*Primary Examiner* — Idowu O Osifade
(74) *Attorney, Agent, or Firm* — Garg Law Firm, PLLC; Rakesh Garg; Anthony Curro

(57) ABSTRACT

A first series of images of a first fluid is received. A first set of fluid characteristics of the first fluid is determined from the first series of images. A second series of images of a second fluid is received. A second set of fluid characteristics of the second fluid is determined from the second series of images. A match is determined to be found between the first set of fluid characteristics and the second set of fluid characteristics. The second fluid is identified based upon determining that the first set of fluid characteristics matches the second set of fluid characteristics.

20 Claims, 9 Drawing Sheets

(56) References Cited

U.S. PATENT DOCUMENTS

2018/0283149 A1* 10/2018 Vittoratos ............... E21B 43/20
2019/0162711 A1*  5/2019 Gaemers ............ G01N 33/2888

OTHER PUBLICATIONS

Lee, S. A., & Yang, C. (2014). A smartphone-based chip-scale microscope using ambient illumination. Lab on a Chip, 14(16), pp. 3056-3063.

Dos Santos et al., Digital image analysis—an alternative tool for monitoring milk authenticity, Analytical Methods, vol. 5, No. 15, May 1, 2013.

Milanez et al., Classification of extra virgin olive oil and verification of adulteration using digital images and discriminant analysis, Analytical Methods, vol. 7, No. 20, Jan. 1, 2015.

PCT, International Searching Authority, PCT/EP2018/082497, Mar. 12, 2019.

\* cited by examiner

DISTINGUISHING FLUIDS BASED UPON DETERMINATION AND ANALYSIS OF DIGITAL IMAGE COLOR SPACE CHARACTERISTICS

TECHNICAL FIELD

The present invention relates generally to a method, system, and computer program product for distinguishing between fluids. More particularly, the present invention relates to a method, system, and computer program product for distinguishing fluids based upon determination and analysis of digital image color space characteristics.

BACKGROUND

Currently a large number of smart phone users exist around the world. Many of these smart phones are provided with high computing power, video streaming capabilities, high quality image capture capabilities and other processing capabilities. This presents an unprecedented opportunity for developing applications based on these capabilities, especially for sensing and imaging applications. One field of technology in which there is a need to provide for low-cost and high-performance analysis and/or analysis is that of fluid identification or verification. For example, the oil industry is interested in detecting the identity of and/or verifying the authenticity of motor oils. For example, the oil industry is interested in verifying the authenticity of a sample of motor oil as well as detecting any contamination that the motor oil may contain. Another example is the wine industry interested in identifying or verifying the authenticity of wine a customer buys in a market.

SUMMARY

The illustrative embodiments provide a method, system, and computer program product. An embodiment of a method for verifying an authenticity of a fluid includes receiving a first series of images of a first fluid, and determining a first set of fluid characteristics of the first fluid from the first series of images. The embodiment further includes receiving a second series of images of a second fluid, and determining a second set of fluid characteristics of the second fluid from the second series of images. The embodiment further includes determining that a match is found between the first set of fluid characteristics and the second set of fluid characteristics. The embodiment still further includes identifying the second fluid based upon determining that the first set of fluid characteristics matches the second set of fluid characteristics. Thus, the embodiment provides a solution to existing problems inherent in analyzing fluids by providing for digital image identification of fluids to distinguish different liquids or other fluids by digital image characteristics.

An embodiment further includes training a machine learning classifier based upon the first set of fluid characteristics. In an embodiment, determining that the match is found between the first set of fluid characteristics and the second set of fluid characteristics is based on the second set of fluid characteristics being processed by the machine learning classifier.

In an embodiment, determining that a match is found between the first set of fluid characteristics and the second set of fluid characteristics includes determining that the first set of fluid characteristics matches the second set of fluid characteristics within a predetermined threshold value.

In an embodiment, the first set of fluid characteristics includes color space characteristics of the first fluid and the second set of fluid characteristics of the second fluid includes color space characteristics of the second fluid. In an embodiment, the color space characteristics of the first fluid and the second fluid include at least one of a hue distribution and a saturation distribution of the first fluid and the second fluid.

In an embodiment, the first set of fluid characteristics of the first fluid further includes a viscosity of the first fluid and the second set of fluid characteristics of the second fluid further includes a viscosity of the second fluid. An embodiment further includes determining the viscosity of the first fluid based upon a Brownian motion pattern detected from the first series of images, and determining the viscosity of the second fluid based upon a Brownian motion pattern detected from the second series of images.

In an embodiment, determining that the match is found between the first set of fluid characteristics and the second set of fluid characteristics further includes matching the viscosity of the first fluid to the viscosity of the second fluid. In an embodiment, the first set of fluid characteristics further includes at least one of a density of particles in the first fluid and a size distribution of particles in the first fluid. In an embodiment, the first set of fluid characteristics further includes a magnetic response of the first fluid, wherein the first series of images includes at least one image obtained before application of a magnetic force to the first fluid and at least one image obtained after application of the magnetic force to the first fluid.

An embodiment includes a computer usable program product. The computer usable program product includes one or more computer-readable storage devices, and program instructions stored on at least one of the one or more storage devices.

An embodiment includes a computer system. The computer system includes one or more processors, one or more computer-readable memories, and one or more computer-readable storage devices, and program instructions stored on at least one of the one or more storage devices for execution by at least one of the one or more processors via at least one of the one or more memories.

BRIEF DESCRIPTION OF THE DRAWINGS

Certain novel features characteristic of the invention are set forth in the appended claims. The invention itself, however, as well as a preferred mode of use, further objectives and advantages thereof, will best be understood by reference to the following detailed description of the illustrative embodiments when read in conjunction with the accompanying drawings, wherein:

DETAILED DESCRIPTION

Figure 1:
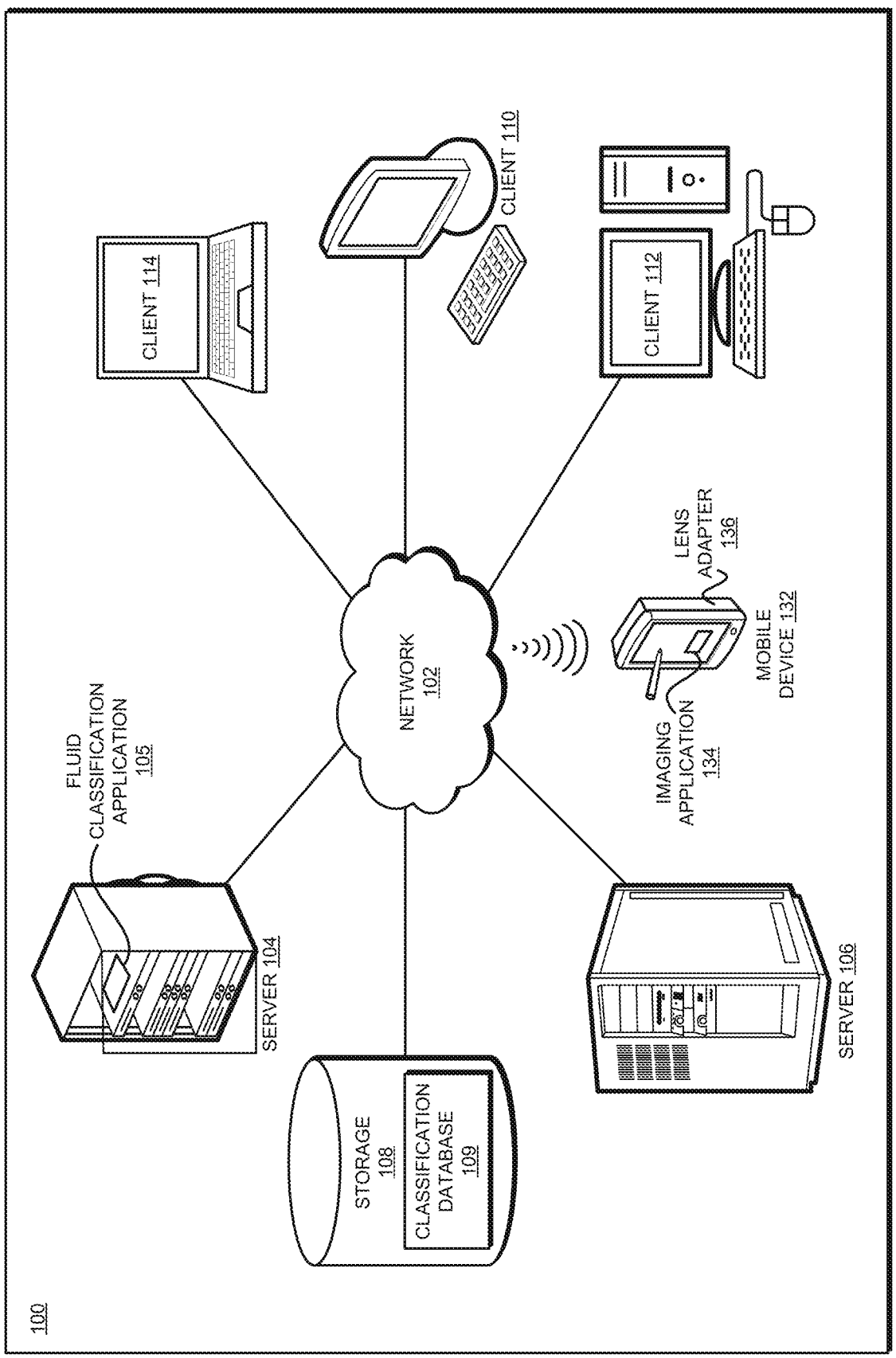
FIG. 1 depicts a block diagram of a network of data processing systems in which illustrative embodiments may be implemented.

Various embodiments include a method, system, and computer program product for distinguishing fluids based upon determination and analysis of color space characteristics of a series of digital images of a fluid. Many industries, such as the petroleum industry, are interested in detecting or authenticating fluids and/or detecting any contamination that the fluids may contain. Existing procedures for analysis of fluids such as motor oil are often costly requiring chemical analysis or costly imaging system. Various embodiments described herein provide for one or more advantages of using low-cost hardware, such as a smartphone, having an imaging device incorporated therewith to provide image processing of images of fluids to identify and/or authenticate the fluids. Various embodiments described herein provide a solution to existing problems inherent in analyzing fluids by providing for digital image identification of fluids using low-cost imaging hardware or other suitable computing devices attached to suitable image capturing hardware to distinguish different liquids or other fluids by digital image characteristics such as color. In some embodiments, detecting of contamination within a fluid is provided to detect adulterated fluids.

In an embodiment, an application receives a first series of images of a first fluid, such as an oil sample, captured using an imaging device, such as a smartphone or other mobile device. In the embodiment, the application determines a set of characteristics of the first fluid based on the series of images. In a particular embodiment, the first set of images of the first fluid are representative of a reference fluid to which a target fluid is to be compared at a later time. In one or more embodiments, the set of characteristics includes a set of color space characteristics of the series of images. A color space is a mathematical model of a representation of colors in a digital image represented as tuples of numbers. In a particular embodiment, the color space includes a Hue, Saturation, Value (HSV) color space in which the set of color space characteristics includes a distributions of hue, space, and value characteristics of the series of digital images.

A hue of a color describes which pure color (e.g., red, yellow, green, and blue) the color resembles, saturation of a color describes the intensity of the color (e.g., the amount of white present in the color), and value describes the brightness of the color. In particular embodiments, the application determines distributions of hue, saturation, and value within the series of images of the fluid.

In an embodiment, the imaging device is configured to include a lens adapter having a microlens contained therein to enable high resolution image capture of the fluid using the imaging device. In particular embodiments, the microlens enables image capture of micron sized (millionth of a meter) objects using a mobile device having high magnification of, for example, 15× or larger (for comparison a human hair width is 100 micron). Various embodiments provide for enhanced determination of color space characteristics of an image of a fluid using the microlens. In other particular embodiments, microbeads are added to the fluid and the application is configured to track microbead motion in the series of images due to a Brownian motion pattern of the fluid to determine viscosity values of the fluid as a further characteristic in the set of characteristics. The microbeads can sample the viscosity of micro environments and can therefore detect any adulteration or other inhomogeneity in the liquid by tracking the motion of plurality of microbeads. The Brownian motion pattern includes a positional shift of each of a plurality of particles (e.g., microbeads) within the fluid. Distributions of positional shifts of a plurality of beads conforms to a Gaussian shape from which a number of parameters associated with microbead motion like Diffusion coefficient and viscosity can be obtained. In a particular embodiment, the first set of characteristics further includes at least one of a density of particles in the first fluid and a size distribution of particles in the first fluid. In another particular embodiment, the set of characteristics further includes a magnetic response of the first fluid in which the series of images includes images taken before and after application of a magnetic force to the fluid.

In the embodiment, the application stores the distributions of the color space characteristics of the first series of images within a classification database in association with the first fluid. In particular embodiments, the application stores hue and saturation value distributions of the series of images in association with the first fluid. In other particular embodiments, the application further stores the viscosity values of the first fluid in the classification database in association with the first fluid.

In the embodiment, the application receives a second series of images of a second fluid. In a particular embodiment, the second series of images is a target fluid for which an identity or authentication is to be performed with respect to the first fluid. In the embodiment, the application determines a second set of color space characteristics, such as HSV distributions, of the second series of images of the second fluid. In particular embodiments, the second set of color space characteristics may further include a viscosity of the second fluid. In the embodiment, the application compares the second set of color space characteristics of the second series of images to the first set of color space characteristics of the first set of images stored in the classification database to determine if a match is found within a predetermined threshold value. In a particular embodiment, the application compares histograms of the hue and saturation distributions of the first set of color space characteristics and the second set of color space characteristics to determine if a match is found. In the embodiment, if the application determines that a match is found within the predetermined threshold value, the application authenticates the second fluid as being the same as the first fluid. If the application determines that a match is not found, the application indicates that the second fluid is not authenticated as being the same as the first fluid.

In another embodiment, application uses the determined first set of color space characteristics of the first fluid to train a machine learning classifier, and the second fluid is classified based upon the second set of color space characteristics and the classifier to determine whether the first set of color space characteristics matches the second set of color space characteristics in order to authenticate the second fluid as matching the first fluid. In a particular embodiment, the machine learning classifier includes a convolutional neural network.

Figure 2:
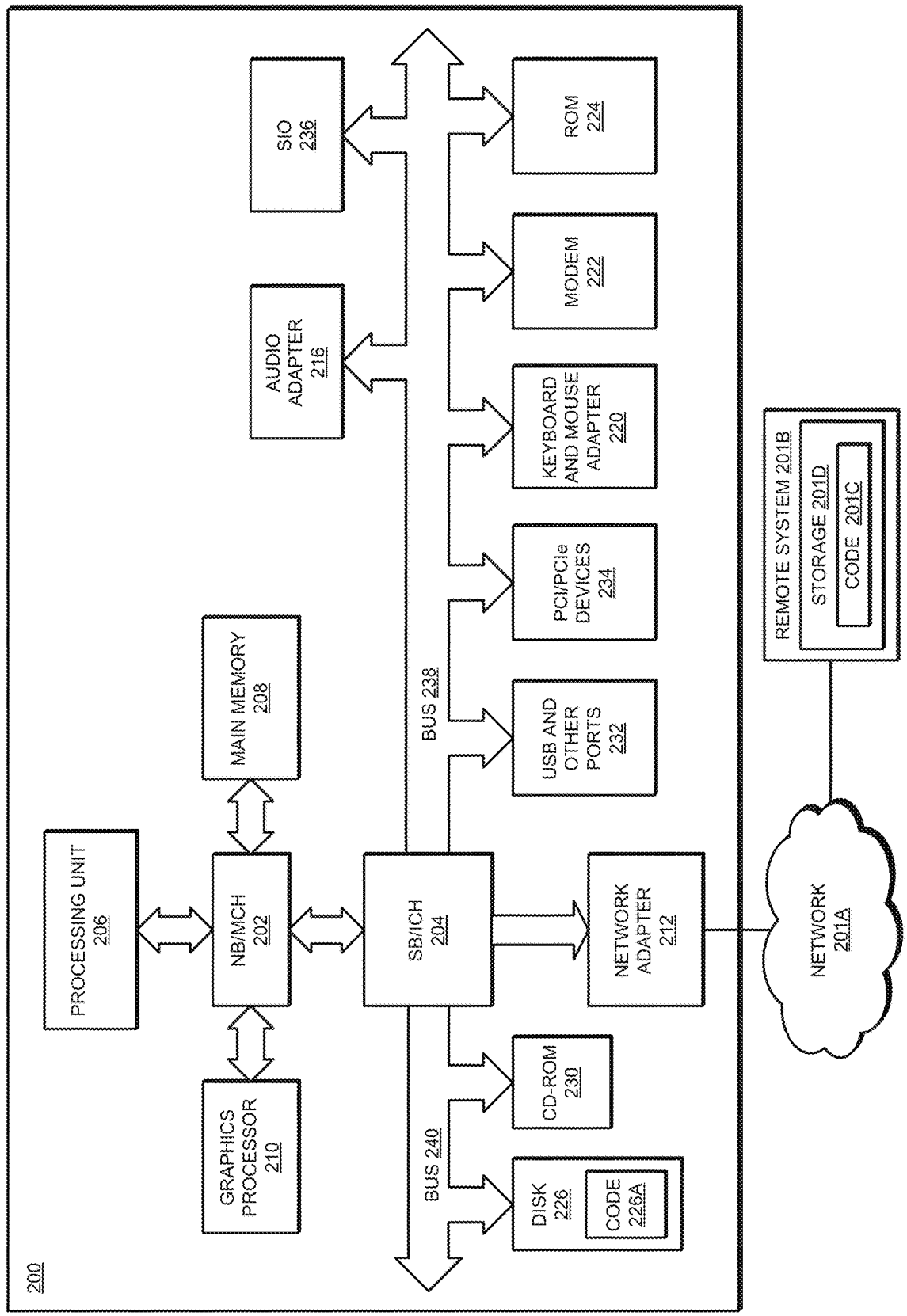
FIG. 2 depicts a block diagram of a data processing system in which illustrative embodiments may be implemented.

With reference to the figures and in particular with reference to FIGS. 1 and 2, these figures are example diagrams of data processing environments in which illustrative embodiments may be implemented. FIGS. 1 and 2 are only examples and are not intended to assert or imply any limitation with regard to the environments in which different embodiments may be implemented. A particular implementation may make many modifications to the depicted environments based on the following description.

FIG. 1 depicts a block diagram of a network of data processing systems in which illustrative embodiments may be implemented. Data processing environment 100 is a network of computers in which the illustrative embodiments may be implemented. Data processing environment 100 includes network 102. Network 102 is the medium used to provide communications links between various devices and computers connected together within data processing environment 100. Network 102 may include connections, such as wire, wireless communication links, or fiber optic cables.

Clients or servers are only example roles of certain data processing systems connected to network 102 and are not intended to exclude other configurations or roles for these data processing systems. Server 104 and server 106 couple to network 102 along with storage unit 108. Software applications may execute on any computer in data processing environment 100. Clients 110, 112, and 114 are also coupled to network 102. A data processing system, such as server 104 or 106, or client 110, 112, or 114 may contain data and may have software applications or software tools executing thereon.

Only as an example, and without implying any limitation to such architecture, FIG. 1 depicts certain components that are usable in an example implementation of an embodiment. For example, servers 104 and 106, and clients 110, 112, 114, are depicted as servers and clients only as example and not to imply a limitation to a client-server architecture. As another example, an embodiment can be distributed across several data processing systems and a data network as shown, whereas another embodiment can be implemented on a single data processing system within the scope of the illustrative embodiments. Data processing systems 104, 106, 110, 112, and 114 also represent example nodes in a cluster, partitions, and other configurations suitable for implementing an embodiment.

Mobile device 132 is an example of a mobile device described herein. For example, mobile device 132 can take the form of a smartphone, a tablet computer, a laptop computer, client 110 in a stationary or a portable form, a wearable computing device, or any other suitable device. Any software application described as executing in another data processing system in FIG. 1 can be configured to execute in mobile device 132 in a similar manner. Any data or information stored or produced in another data processing system in FIG. 1 can be configured to be stored or produced in device 132 in a similar manner. Mobile device 132 includes an imaging application 134 configured to capture one or more images or video sequences of a fluid from a camera of mobile device 132. Mobile device 132 is further coupled to lens adapter 136 to facilitate capture of one or more images or videos sequences of an object through a lens positioned within lens adapter 136. In a particular embodiment, the lens is a microlens as described herein.

Fluid classification application 105 implements an embodiment described herein. For example, fluid classification application 105 performs one or more of the fluid classification operations on a series of images received from mobile device 132 as described herein. In particular embodiments, fluid classification application 105 includes a machine learning classifier. In other particular embodiments, one or more of the fluid classification operations described herein are performed by imaging application 134 of mobile device 132.

Servers 104 and 106, storage unit 108, and clients 110, 112, and 114, and device 132 may couple to network 102 using wired connections, wireless communication protocols, or other suitable data connectivity. Clients 110, 112, and 114 may be, for example, personal computers or network computers. Storage device 108 includes a classification database 109 configured to store a set of color space characteristics of a series of images to be used in classifying a fluid as described in various embodiments herein.

In the depicted example, server 104 may provide data, such as boot files, operating system images, and applications to clients 110, 112, and 114. Clients 110, 112, and 114 may be clients to server 104 in this example. Clients 110, 112, 114, or some combination thereof, may include their own data, boot files, operating system images, and applications. Data processing environment 100 may include additional servers, clients, and other devices that are not shown.

In the depicted example, data processing environment 100 may be the Internet. Network 102 may represent a collection of networks and gateways that use the Transmission Control Protocol/Internet Protocol (TCP/IP) and other protocols to communicate with one another. At the heart of the Internet is a backbone of data communication links between major nodes or host computers, including thousands of commercial, governmental, educational, and other computer systems that route data and messages. Of course, data processing environment 100 also may be implemented as a number of different types of networks, such as for example, an intranet, a local area network (LAN), or a wide area network (WAN). FIG. 1 is intended as an example, and not as an architectural limitation for the different illustrative embodiments.

Among other uses, data processing environment 100 may be used for implementing a client-server environment in which the illustrative embodiments may be implemented. A client-server environment enables software applications and data to be distributed across a network such that an application functions by using the interactivity between a client data processing system and a server data processing system. Data processing environment 100 may also employ a service oriented architecture where interoperable software components distributed across a network may be packaged together as coherent business applications. Data processing environment 100 may also take the form of a cloud, and employ a cloud computing model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service.

With reference to FIG. 2, this figure depicts a block diagram of a data processing system in which illustrative embodiments may be implemented. Data processing system 200 is an example of a computer, such as servers 104 and 106, or clients 110, 112, and 114 in FIG. 1, or another type of device in which computer usable program code or instructions implementing the processes may be located for the illustrative embodiments.

Data processing system 200 is also representative of a data processing system or a configuration therein, such as data processing system 132 in FIG. 1 in which computer usable program code or instructions implementing the processes of the illustrative embodiments may be located. Data processing system 200 is described as a computer only as an example, without being limited thereto. Implementations in the form of other devices, such as device 132 in FIG. 1, may modify data processing system 200, such as by adding a touch interface, and even eliminate certain depicted components from data processing system 200 without departing from the general description of the operations and functions of data processing system 200 described herein.

In the depicted example, data processing system 200 employs a hub architecture including North Bridge and memory controller hub (NB/MCH) 202 and South Bridge and input/output (I/O) controller hub (SB/ICH) 204. Processing unit 206, main memory 208, and graphics processor 210 are coupled to North Bridge and memory controller hub (NB/MCH) 202. Processing unit 206 may contain one or more processors and may be implemented using one or more heterogeneous processor systems. Processing unit 206 may be a multi-core processor. Graphics processor 210 may be coupled to NB/MCH 202 through an accelerated graphics port (AGP) in certain implementations.

In the depicted example, local area network (LAN) adapter 212 is coupled to South Bridge and I/O controller hub (SB/ICH) 204. Audio adapter 216, keyboard and mouse adapter 220, modem 222, read only memory (ROM) 224, universal serial bus (USB) and other ports 232, and PCI/PCIe devices 234 are coupled to South Bridge and I/O controller hub 204 through bus 238. Hard disk drive (HDD) or solid-state drive (SSD) 226 and CD-ROM 230 are coupled to South Bridge and I/O controller hub 204 through bus 240. PCI/PCIe devices 234 may include, for example, Ethernet adapters, add-in cards, and PC cards for notebook computers. PCI uses a card bus controller, while PCIe does not. ROM 224 may be, for example, a flash binary input/output system (BIOS). Hard disk drive 226 and CD-ROM 230 may use, for example, an integrated drive electronics (IDE), serial advanced technology attachment (SATA) interface, or variants such as external-SATA (eSATA) and micro-SATA (mSATA). A super I/O (SIO) device 236 may be coupled to South Bridge and I/O controller hub (SB/ICH) 204 through bus 238.

Memories, such as main memory 208, ROM 224, or flash memory (not shown), are some examples of computer usable storage devices. Hard disk drive or solid state drive 226, CD-ROM 230, and other similarly usable devices are some examples of computer usable storage devices including a computer usable storage medium.

An operating system runs on processing unit 206. The operating system coordinates and provides control of various components within data processing system 200 in FIG. 2. The operating system may be a commercially available operating system for any type of computing platform, including but not limited to server systems, personal computers, and mobile devices. An object oriented or other type of programming system may operate in conjunction with the operating system and provide calls to the operating system from programs or applications executing on data processing system 200.

Instructions for the operating system, the object-oriented programming system, and applications or programs, such as application 105 in FIG. 1, are located on storage devices, such as in the form of code 226A on hard disk drive 226, and may be loaded into at least one of one or more memories, such as main memory 208, for execution by processing unit 206. The processes of the illustrative embodiments may be performed by processing unit 206 using computer implemented instructions, which may be located in a memory, such as, for example, main memory 208, read only memory 224, or in one or more peripheral devices.

Furthermore, in one case, code 226A may be downloaded over network 201A from remote system 201B, where similar code 201C is stored on a storage device 201D. in another case, code 226A may be downloaded over network 201A to remote system 201B, where downloaded code 201C is stored on a storage device 201D.

The hardware in FIGS. 1-2 may vary depending on the implementation. Other internal hardware or peripheral devices, such as flash memory, equivalent non-volatile memory, or optical disk drives and the like, may be used in addition to or in place of the hardware depicted in FIGS. 1-2. In addition, the processes of the illustrative embodiments may be applied to a multiprocessor data processing system.

In some illustrative examples, data processing system 200 may be a personal digital assistant (PDA), which is generally configured with flash memory to provide non-volatile memory for storing operating system files and/or user-generated data. A bus system may comprise one or more buses, such as a system bus, an I/O bus, and a PCI bus. Of course, the bus system may be implemented using any type of communications fabric or architecture that provides for a transfer of data between different components or devices attached to the fabric or architecture.

A communications unit may include one or more devices used to transmit and receive data, such as a modem or a network adapter. A memory may be, for example, main memory 208 or a cache, such as the cache found in North Bridge and memory controller hub 202. A processing unit may include one or more processors or CPUs.

The depicted examples in FIGS. 1-2 and above-described examples are not meant to imply architectural limitations. For example, data processing system 200 also may be a tablet computer, laptop computer, or telephone device in addition to taking the form of a mobile or wearable device.

Where a computer or data processing system is described as a virtual machine, a virtual device, or a virtual component, the virtual machine, virtual device, or the virtual component operates in the manner of data processing system 200 using virtualized manifestation of some or all components depicted in data processing system 200. For example, in a virtual machine, virtual device, or virtual component, processing unit 206 is manifested as a virtualized instance of all or some number of hardware processing units 206 available in a host data processing system, main memory 208 is manifested as a virtualized instance of all or some portion of main memory 208 that may be available in the host data processing system, and disk 226 is manifested as a virtualized instance of all or some portion of disk 226 that may be available in the host data processing system. The host data processing system in such cases is represented by data processing system 200.

Figure 3:
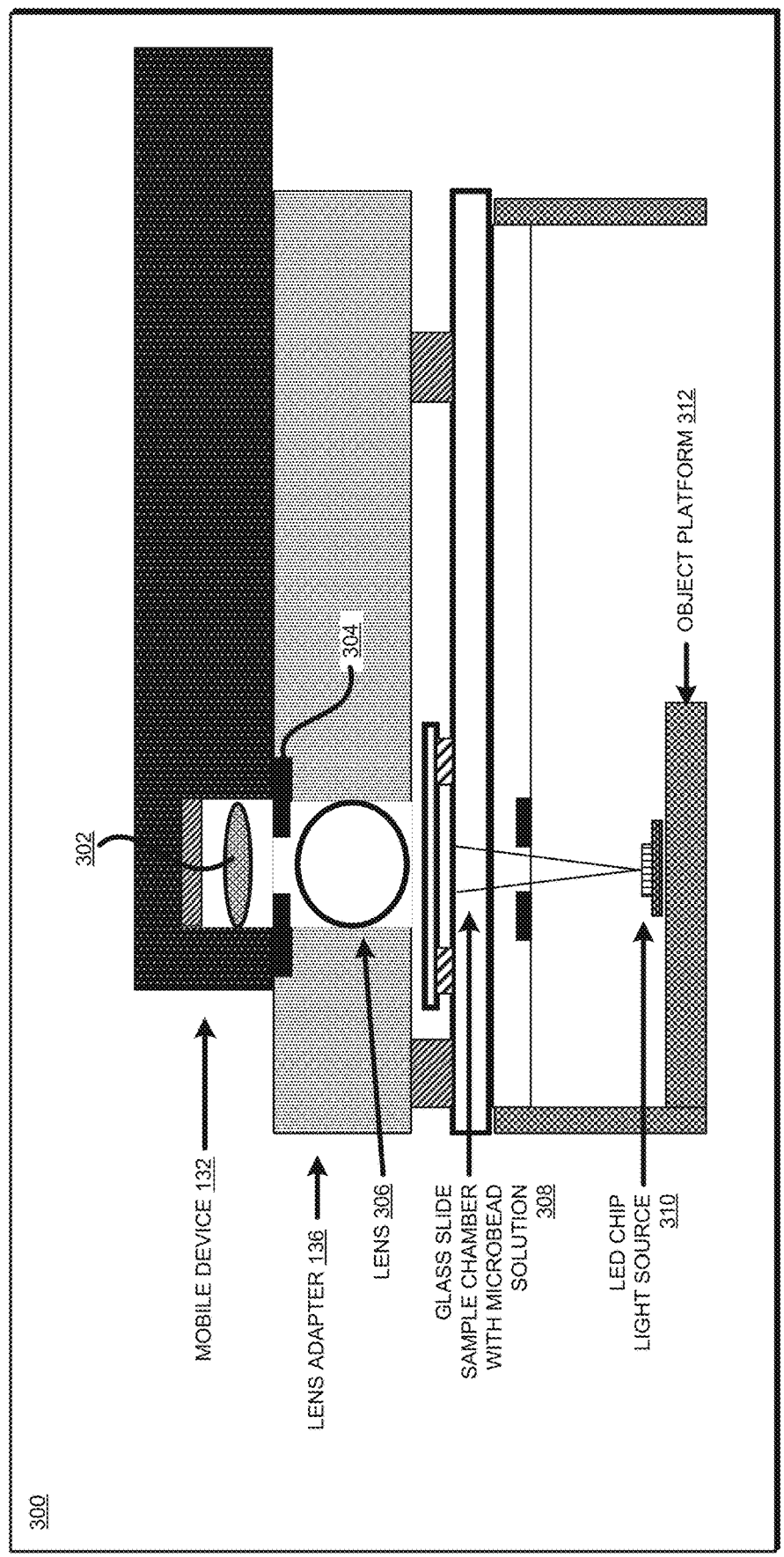
FIG. 3 depicts an example configuration in which a lens adapter is used for imaging fluids according to an embodiment.

With reference to FIG. 3, this figure depicts an example configuration 300 in which lens adapter 136 is used for imaging fluids according to an embodiment. In the example configuration of FIG. 3, mobile device 132 is coupled to lens adapter 136 with camera lens 302 of mobile device 132 in alignment with an aperture of a lens adapter holder insert 304 and a lens 306. In a particular embodiment, lens 306 is a microlens having a resolution of less than or equal to one micrometer. The example configuration 300 further includes a fluid sample 308 in alignment with lens 306. In the illustrated example of FIG. 3, fluid sample 308 is a glass slide sample chamber including a microbead solution. In another particular embodiment, fluid sample 308 is a vial containing a fluid such as oil. In still another embodiment, a film of photonic crystal may be applied to the fluid sample 308, such as on a surface of a glass slide, to further enhance color selectivity of determining the color space characteristics of the fluid in which the film of photonic crystal functions as a highly selective color filter.

Example configuration 300 further includes a light source 310 positioned below fluid sample 308 upon an object platform 312. Light source 310 is configured to direct light upon and/or illuminate fluid sample 308 upward toward lens 306 and camera lens 302. In a particular embodiment, light source 310 is a light emitting diode (LED) chip light source. In the embodiment, mobile device 132 is configured to capture still images and/or video images of fluid sample 308 through lens 306 such that the images of fluid sample 308 are magnified when captured.

By locating the positions of microbeads in the video frames of images recorded with mobile device 132 according to the illustrative embodiment, microbead positions in subsequent frames can be tracked. By calculating the microbead position distributions, a viscosity of fluid sample 308 can be determined.

Figure 4:
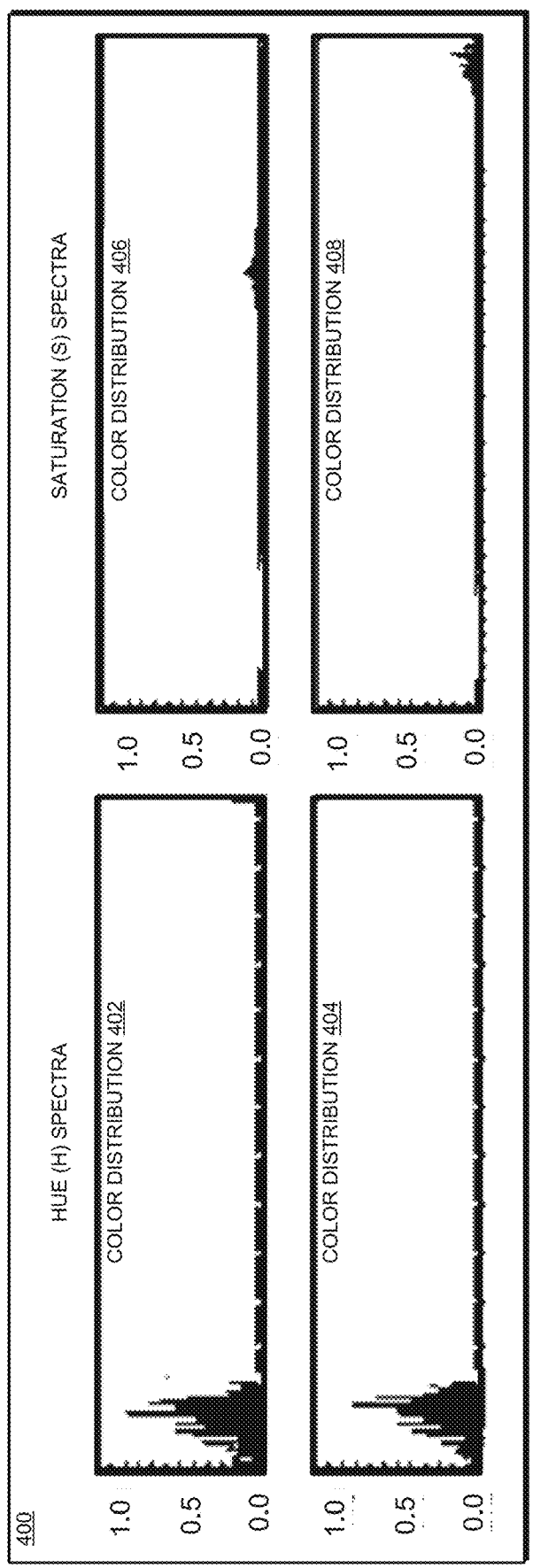
FIG. 4 depicts an example of hue and saturation distributions of a first series of images of a first fluid and a second series of images of a second fluid according to an embodiment.

With reference to FIG. 4, this figure depicts an example of hue and saturation distributions of a first series of images of a first fluid and a second series of images of a second fluid according to an embodiment. In the particular example of FIG. 4, the first series of images and second series of images are obtained without the use of a microlens. As can be seen in FIG. 4, differences between a first hue distribution 402 of the first series of images and a second hue distribution 404 of the second series are not as pronounced as differences between a first saturation distribution 406 of the first series of images and a second saturation distribution 408 of the second series of images. Accordingly, comparing first saturation distribution 406 of second saturation distribution 408 may facilitate identification and/or authentication of a fluid.

Figure 5:
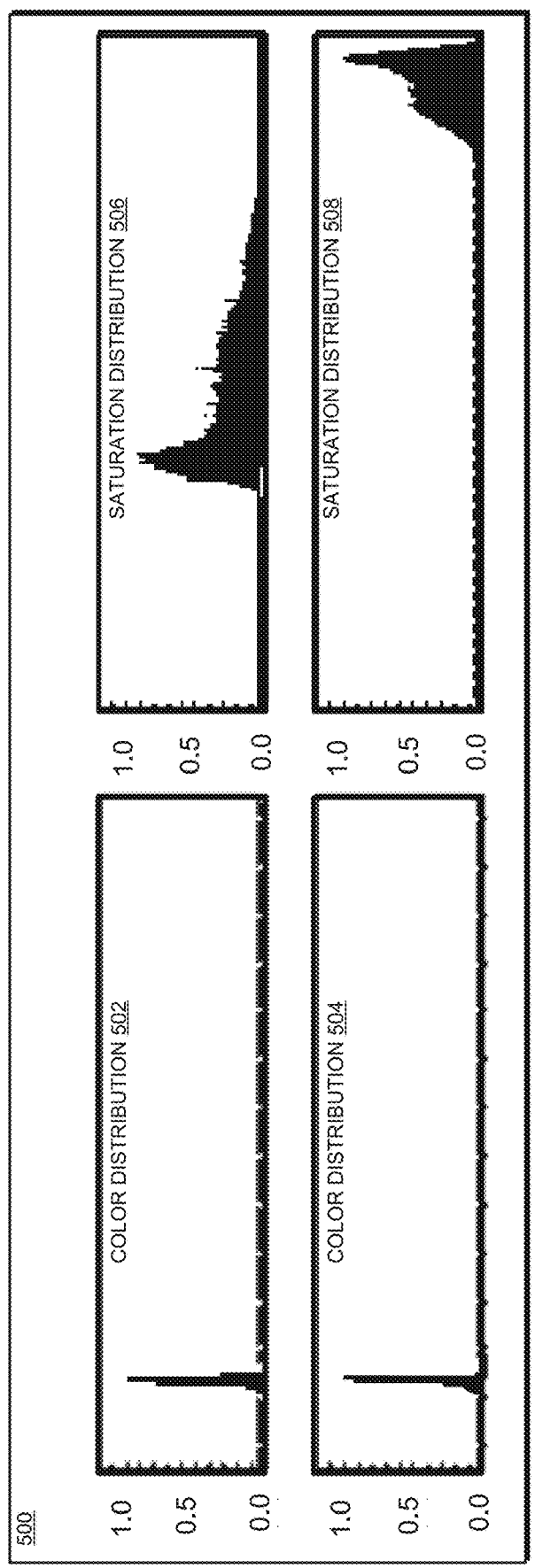
FIG. 5 depicts another example of hue and saturation distributions of a first series of images of a first fluid and a second series of images of a second fluid according to an embodiment.

With reference to FIG. 5, this figure depicts another example of hue and saturation distributions of a first series of images of a first fluid and a second series of images of a second fluid according to an embodiment. In the particular example of FIG. 5, the first series of images and second series of images are obtained with the use of a microlens. As can be seen in FIG. 5, differences between a first hue distribution 502 of the first series of images and a second hue distribution 504 of the second series are not as pronounced whereas differences between a first saturation distribution 506 of the first series of images and a second saturation distribution 508 of the second series of images are greatly enhanced such that peaks of first saturation distribution 507 and second distribution 508 have practically no overlap thus greatly improving the capability of distinguishing the first fluid and the second fluid. In a particular embodiment, a machine-learning classifier is built based on differences between the hue-saturation spectra composition. In some situations, the differences between the hue-saturation spectra composition are dependent upon a lighting condition during image capture. In particular embodiments, the classifier is trained with different lighting environment for the same fluid sample to facilitate subsequent comparison of a fluid to the reference fluid.

Figure 6:
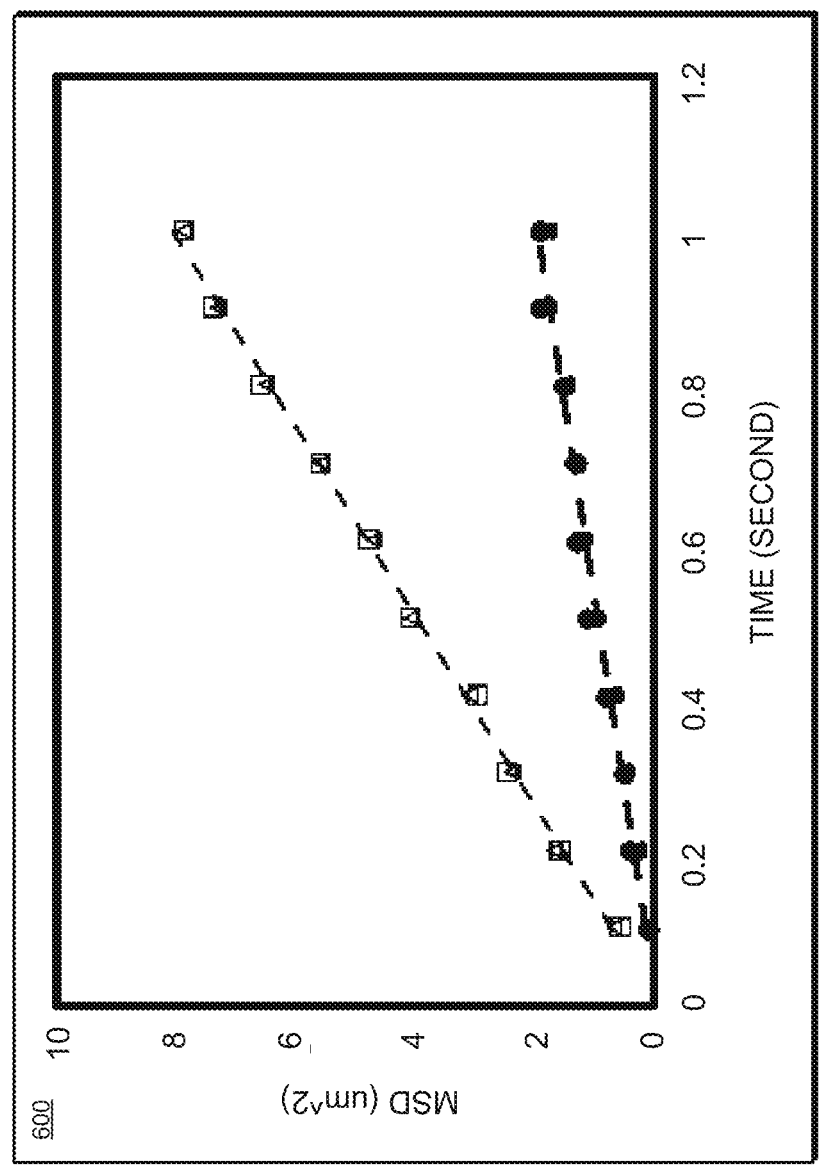
FIG. 6 depicts an example simulated plot of mean-square displacement (MSD) for a microbead in high and low viscosity media according to an embodiment.

Referring now to FIG. 6, this figure depicts an example simulated plot 600 of mean-square displacement (MSD) for a microbead in high and low viscosity media according to an embodiment.

Brownian motion of microscopic particles such as polymer microbeads and other colloidal particles can be observed in liquid or air due to the random motion of the molecules in the medium in which they are embedded. As these small molecules constantly collide with larger particles embedded in the medium, at any moment there is imbalance in the net force impacted by these small molecules on the larger particles. The imbalance in the net force results in the random movement of the larger particles. Polymer beads in a size range of 0.05 micrometers to a few micrometers fall within a convenient range for observation. The Brownian motion of particles in three dimensions is well described by an equation for mean-square displacement (MSD):

$$\delta x^2 = 6Dt \qquad (1)$$

where t is elapsed time. If the positions of a particle over different times $t_1, t_2, t_3, \ldots t_n$ is known, then MSD can be calculated from the equation:

$$\delta x^2 = \frac{[(x(t_1) - x(t_0))^2 + (x(t_2) - x(t_1))^2 + \ldots + (x(t_n) - x(t_{n-1}))^2]}{n} \qquad (2)$$

where the time interval, $\delta t = t_n - t_{n-1}$, is the same between different snap-shots of the particle. Therefore by following particle trajectories over time one can obtain their diffusion constant D that characterizes the particle motion can be obtained.

For a spherical particle, combining the stokes law for the drag force and Einstein's relation, one obtains:

$$D = \frac{k_B T}{6\pi \eta r} \qquad (3)$$

where 'r' is the radius of the particle, 'η' is the dynamic viscosity of the medium (liquid), '$k_B$' is the Boltzmann constant, and 'T' is the temperature of the medium. It follows by determining the diffusion coefficient experimentally and knowing the average particle radius the above equation can be used to obtain the viscosity of the medium. Still referring to FIG. 6, FIG. 6 shows a MSD plot for Brownian motion in fluids of two different viscosities. Indeed as the microbeads explore regions of size in tens of micrometers, it can sample the microenvironment in the liquid under investigation offering a powerful means to detect contaminants at the micron scale.

Figure 7:
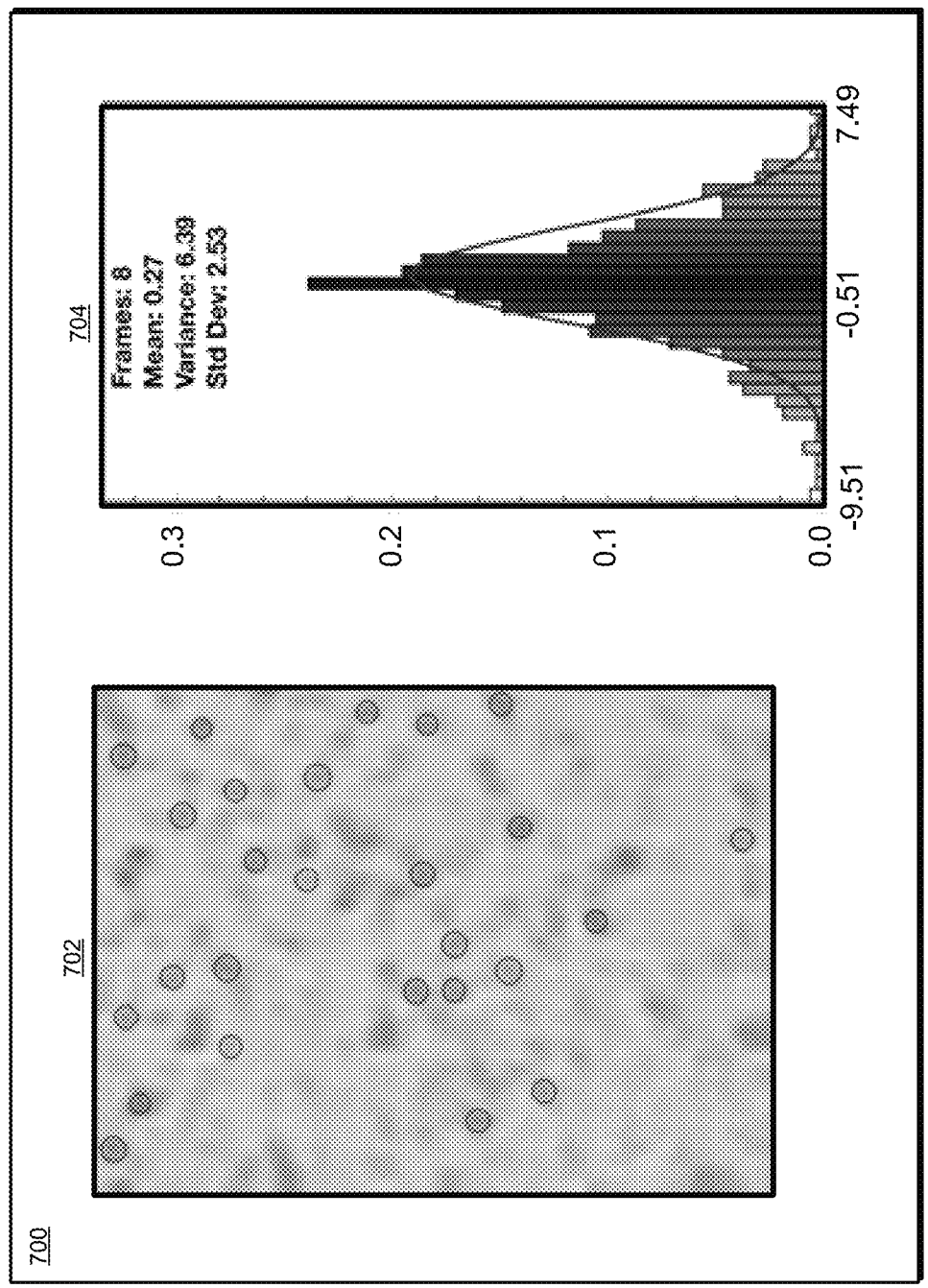
FIG. 7 depicts an example of microbead detection and tracking for determining fluid viscosity according to an embodiment.

Referring now to FIG. 7, this figure depicts an example of microbead detection and tracking for determining fluid viscosity according to an embodiment. In the particular example of FIG. 7, microbead detection 702 is performed on one or more images of a fluid to determine a positional shift distribution 704 indicative of a viscosity of the fluid. By detecting microbead positions in a series of images or video frames of the fluid and tracking the motion of the microbeads in subsequent frames, the application determines positional shifts of the microbeads over different frames to determine Gaussian shape characteristics of Brownian motion of the microbeads. The Gaussian shape characteristics of a particular fluid can be added to training of the classifier to facilitate identification of a fluid using color space characteristics, such as hue and saturation, as well as viscosity characteristics.

Figure 8:
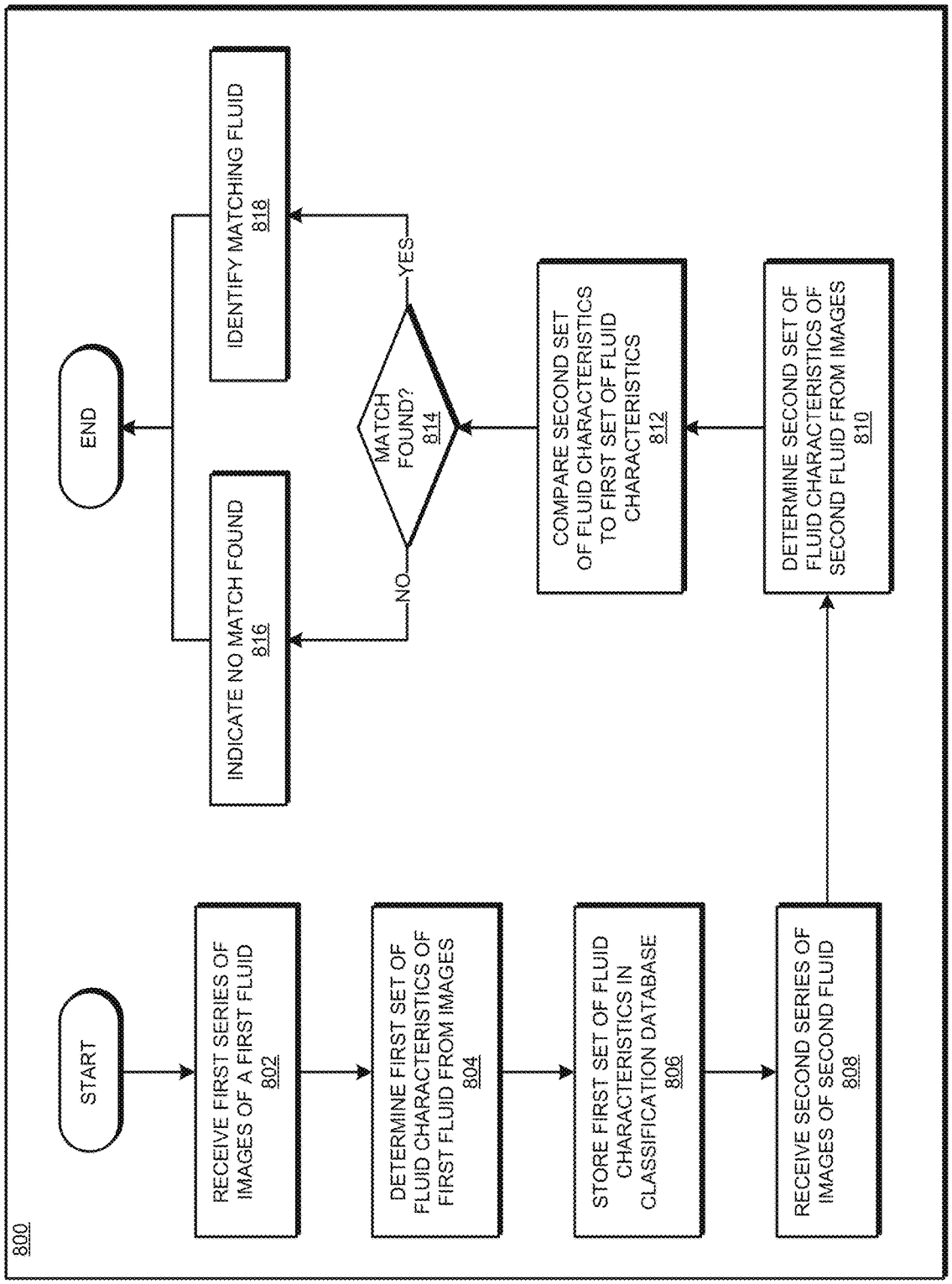
FIG. 8 depicts a flowchart of an example process for distinguishing fluids based upon determination and analysis of color space characteristics of a series of digital images of a fluid in accordance with an illustrative embodiment.

With reference to FIG. 8, this figure depicts a flowchart of an example process 800 for distinguishing fluids based upon determination and analysis of color space characteristics of a series of digital images of a fluid in accordance with an illustrative embodiment. In 802, fluid classification application 105 receives a first series of images of a first fluid, such as an oil sample, captured using an imaging device, such as mobile device 132. In 804, fluid classification application 105 determines a set of fluid characteristics of the first fluid based on the first series of images.

In a particular embodiment, the first set of images of the first fluid are representative of a reference fluid to which a target fluid is to be compared at a later time. In one or more embodiments, the set of fluid characteristics includes a set of color space characteristics of the series of images. In a particular embodiment, the color space includes HSV color space in which the set of color space characteristics includes distributions of hue, space, and value characteristics of the series of digital images. In other embodiments, a different color space may be used such as a red-green-blue (RGB) color space. In particular embodiments, fluid classification application 105 determines distributions of hue and saturation within the first series of images of the first fluid.

In a particular embodiments, microbeads are added to the fluid and fluid classification application 105 is configured to track microbead motion in the series of images due to a Brownian motion pattern of the fluid to determine a viscosity of the fluid as a further characteristic in the set of characteristics. The Brownian motion pattern includes a positional shift of each of a plurality of particles (e.g., microbeads) within the fluid. In a particular embodiment, the first set of characteristics further includes at least one of a density of particles in the first fluid and a size distribution of particles in the first fluid. In another particular embodiment, the set of characteristics further includes a magnetic response of the first fluid in which the series of images includes images taken before and after application of a magnetic force to the fluid.

In 806, fluid classification application 105 stores the first set of fluid characteristics of the first series of images within classification database 109 in association with the first fluid. In one embodiment, fluid classification application 105 stores the first set of fluid characteristics of the first series of images within one or more lookup tables. In particular embodiments, fluid classification application 105 stores hue and saturation value distributions of the series of images in association with the first fluid. In other particular embodiments, fluid classification application 105 further stores the viscosity of the first fluid in the classification database in association with the first fluid.

In 808, fluid classification application 105 receives a second series of images of a second fluid. In a particular embodiment, the second series of images is a target fluid for which an identity, authentication, or other distinguishing of the second fluid is to be performed with respect to the first fluid. In 810, fluid classification application 105 determines a second set of fluid characteristics, such as HSV distributions, of the second series of images of the second fluid. In particular embodiments, the second set of color space characteristics may further include a viscosity of the second fluid determined from the second series of images by fluid classification application 105.

In 812, fluid classification application 105 compares the second set of fluid characteristics of the second series of images to the first set of fluid characteristics of the first set of images stored in classification database 109. In 814, fluid classification application 105 determines whether a match is found between the second set of fluid characteristics of the second series of images and the first set of fluid characteristics of the first set of images within a predetermined threshold. In a particular embodiment, the application compares histograms of the hue and saturation distributions of the first set of fluid characteristics and the second set of fluid characteristics to determine if a match is found within the predetermined threshold.

If fluid classification application 105 determines that a match is not found within the predetermined threshold, in 816 fluid classification application 105 indicates that the second fluid does not match the first fluid and process 800 ends. If fluid classification application 105 determines that a match is found within the predetermined threshold, in 818 fluid classification application 105 identifies the second fluid as matching the first fluid and process 800 ends. In accordance with one or more embodiments, the matching of the second fluid with the first fluid verifies the authenticity of the second fluid. Although various embodiments described herein are described as including a set of fluid characteristics of a first fluid within classification database 109, it should be understood that in other embodiments, classification database 109 includes fluid characteristics of a plurality of reference fluids to enable fluid classification application 105 to identify a particular target fluid from among a number of reference fluids.

Figure 9:
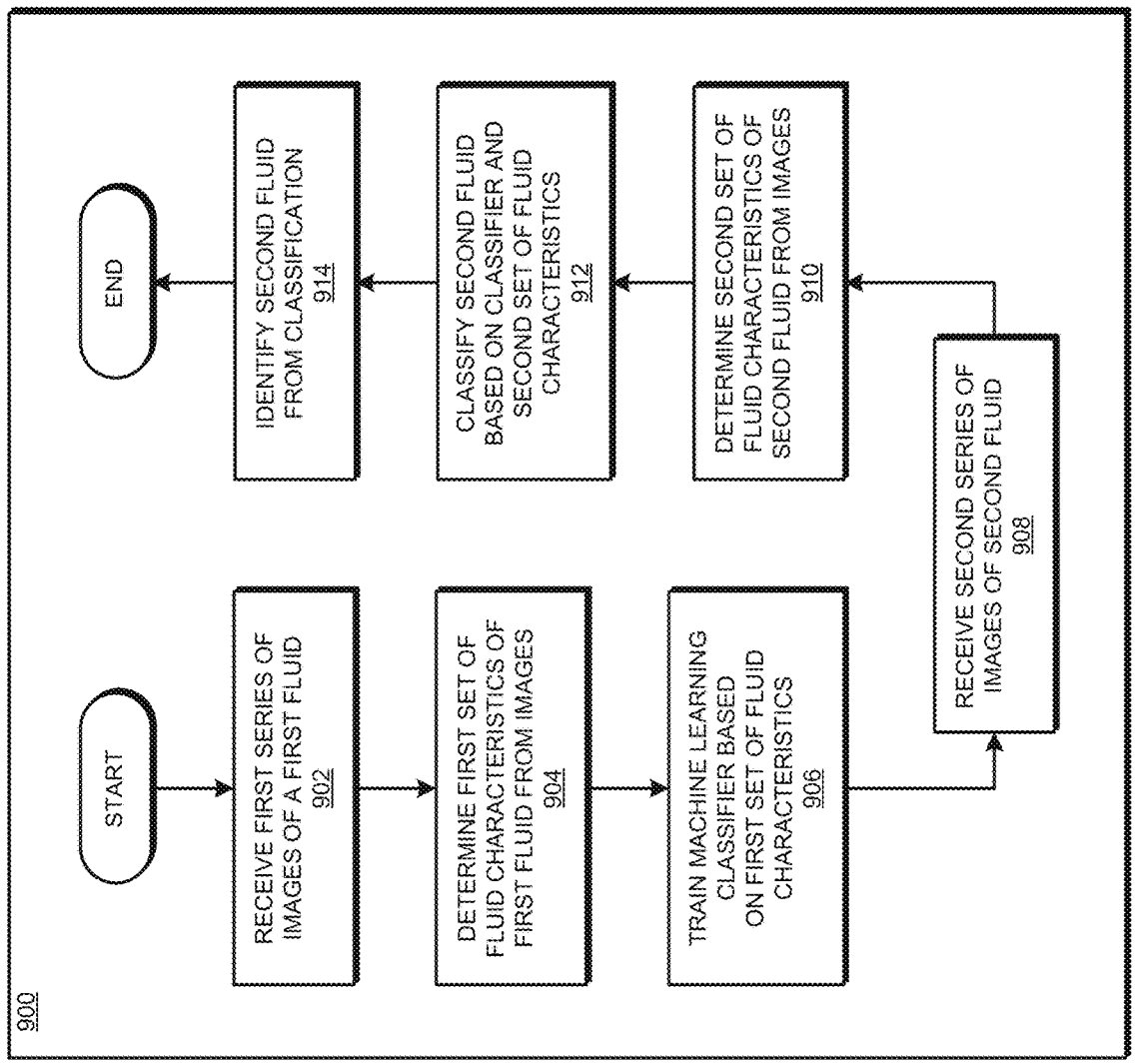
FIG. 9 depicts a flowchart of another example process for distinguishing fluids based upon determination and analysis of color space characteristics of a series of digital images of a fluid in accordance with an illustrative embodiment.

With reference to FIG. 9, this figure depicts a flowchart of another example process 900 for distinguishing fluids based upon determination and analysis of color space characteristics of a series of digital images of a fluid in accordance with an illustrative embodiment. In the embodiment depicted in FIG. 8, a machine-learning classifier is trained and used to authenticate a fluid. In 902, fluid classification application 105 receives a first series of images of a first fluid using an imaging device, such as mobile device 132. In 904, fluid classification application 105 determines a set of fluid characteristics of the first fluid based on the first series of images.

In a particular embodiment, the first set of images of the first fluid are representative of a reference fluid to which a target fluid is to be compared at a later time. In one or more embodiments, the set of fluid characteristics includes a set of color space characteristics of the series of images. In a particular embodiment, the color space includes HSV color space in which the set of color space characteristics includes a distributions of hue, space, and value characteristics of the series of digital images. In other embodiments, a different color space may be used such as a red-green-blue (RGB) color space. In particular embodiments, fluid classification application 105 determines distributions of hue and saturation within the first series of images of the first fluid.

In a particular embodiments, microbeads are added to the fluid and fluid classification application 105 is configured to track microbead motion in the series of images due to a Brownian motion pattern of the fluid to determine a viscosity of the fluid as a further characteristic in the set of characteristics. The Brownian motion pattern includes a positional shift of each of a plurality of particles (e.g., microbeads) within the fluid. In a particular embodiment, the first set of characteristics further includes at least one of a density of particles in the first fluid and a size distribution of particles in the first fluid. In another particular embodiment, the set of characteristics further includes a magnetic response of the first fluid in which the series of images includes images taken before and after application of a magnetic force to the fluid.

In 906, fluid classification application 105 trains a machine-learning classifier with the first set of fluid characteristics of the first series of images in association with the first fluid. In one embodiment, the machine learning classifier includes a convolutional neural network. In other embodiments, other suitable machine learning processes or algorithms may be used to train a fluid classifier. In particular embodiments, fluid classification application 105 trains the classifier using hue and saturation value distributions of the series of images in association with the first fluid. In other particular embodiments, fluid classification application 105 further trains the classifier using the viscosity of the first fluid in association with the first fluid. In a particular embodiment, the machine-learning classifier includes a support vector machine.

In 908, fluid classification application 105 receives a second series of images of a second fluid. In a particular embodiment, the second series of images is a target fluid for which an identity, authentication, or other distinguishing of the second fluid is to be performed with respect to the first fluid. In 910, fluid classification application 105 determines a second set of fluid characteristics, such as HSV distributions, of the second series of images of the second fluid. In particular embodiments, the second set of color space characteristics may further include a viscosity of the second fluid determined from the second series of images by fluid classification application 105.

In 912, fluid classification application 105 provides the second set of fluid characteristics to the machine-learning classifier and the machine-learning classifier predicts if the second fluid is the same or different than the first fluid and classifies the second fluid based on the output of the classifier and the second set of fluid characteristics. In particular embodiments, the machine learning classifier predicts that match is found between the first set of fluid characteristics and the second set of fluid characteristics based on the second set of fluid characteristics being processed by the machine learning classifier.

In 914, fluid classification application 105 identifies, authenticates, and/or validates the second fluid based upon the classification and process 900 ends. Although various embodiments described herein are described as including a set of fluid characteristics of a first fluid to train the classifier, it should be understood that in other embodiments, the classifier is trained with fluid characteristics of a plurality of reference fluids to enable the classifier to identify a particular target fluid from among a number of reference fluids.

Thus, a computer implemented method, system or apparatus, and computer program product are provided in the illustrative embodiments for identifying and distinguishing fluids based upon determination and analysis of digital image color space characteristics and other related features, functions, or operations. Where an embodiment or a portion thereof is described with respect to a type of device, the computer implemented method, system or apparatus, the computer program product, or a portion thereof, are adapted or configured for use with a suitable and comparable manifestation of that type of device.

Where an embodiment is described as implemented in an application, the delivery of the application in a Software as a Service (SaaS) model is contemplated within the scope of the illustrative embodiments. In a SaaS model, the capability of the application implementing an embodiment is provided to a user by executing the application in a cloud infrastructure. The user can access the application using a variety of client devices through a thin client interface such as a web browser (e.g., web-based e-mail), or other light-weight client-applications. The user does not manage or control the underlying cloud infrastructure including the network, servers, operating systems, or the storage of the cloud infrastructure. In some cases, the user may not even manage or control the capabilities of the SaaS application. In some other cases, the SaaS implementation of the application may permit a possible exception of limited user-specific application configuration settings.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method for verifying an authenticity of a fluid, comprising:
    receiving a first series of optical images of a first fluid;
    determining a first set of fluid characteristics of the first fluid from the first series of optical images, a fluid characteristic in the first set of fluid characteristics comprising color space characteristics of the first fluid;
    receiving a second series of optical images of a second fluid;
    determining a second set of fluid characteristics of the second fluid from the second series of optical images, a fluid characteristic in the second set of fluid characteristics comprising color space characteristics of the second fluid;
    determining that a match is found between the first set of fluid characteristics and the second set of fluid characteristics; and
    identifying the second fluid based upon determining that the first set of fluid characteristics matches the second set of fluid characteristics.

2. The method of claim 1, further comprising:
    training a machine learning classifier based upon the first set of fluid characteristics.

3. The method of claim 2, wherein determining that the match is found between the first set of fluid characteristics and the second set of fluid characteristics is based on the second set of fluid characteristics being processed by the machine learning classifier.

4. The method of claim 1, wherein determining that a match is found between the first set of fluid characteristics and the second set of fluid characteristics includes determining that the first set of fluid characteristics matches the second set of fluid characteristics within a predetermined threshold value.

5. The method of claim 1, wherein the first set of fluid characteristics includes color space characteristics of the first fluid and the second set of fluid characteristics of the second fluid includes color space characteristics of the second fluid.

6. The method of claim 5, wherein the color space characteristics of the first fluid and the second fluid include at least one of a hue distribution and a saturation distribution of the first fluid and the second fluid.

7. The method of claim 5, wherein the first set of fluid characteristics of the first fluid further includes a viscosity of the first fluid and the second set of fluid characteristics of the second fluid further includes a viscosity of the second fluid.

8. The method of claim 7, further comprising:
    determining the viscosity of the first fluid based upon a Brownian motion pattern detected from the first series of optical images; and
    determining the viscosity of the second fluid based upon a Brownian motion pattern detected from the second series of optical images.

9. The method of claim 8, wherein determining that the match is found between the first set of fluid characteristics and the second set of fluid characteristics further includes matching the viscosity of the first fluid to the viscosity of the second fluid.

10. The method of claim 8, wherein the first set of fluid characteristics further includes at least one of a density of particles in the first fluid and a size distribution of particles in the first fluid.

11. The method of claim 8, wherein the first set of fluid characteristics further includes a magnetic response of the first fluid, wherein the first series of optical images includes at least one image obtained before application of a magnetic force to the first fluid and at least one image obtained after application of the magnetic force to the first fluid.

12. A computer usable program product comprising one or more computer-readable storage devices, and program instructions stored on at least one of the one or more storage devices, the stored program instructions comprising:

program instructions to receive a first series of optical images of a first fluid;

program instructions to determine a first set of fluid characteristics of the first fluid from the first series of optical images, a fluid characteristic in the first set of fluid characteristics comprising color space characteristics of the first fluid;

program instructions to receive a second series of optical images of a second fluid;

program instructions to determine a second set of fluid characteristics of the second fluid from the second series of optical images, a fluid characteristic in the second set of fluid characteristics comprising color space characteristics of the second fluid;

program instructions to determine that a match is found between the first set of fluid characteristics and the second set of fluid characteristics; and program instructions to identify the second fluid based upon determining that the first set of fluid characteristics matches the second set of fluid characteristics.

13. The computer usable program product of claim 12, further comprising:

program instructions to train a machine learning classifier based upon the first set of fluid characteristics.

14. The computer usable program product of claim 13, wherein determining that the match is found between the first set of fluid characteristics and the second set of fluid characteristics is based on the second set of fluid characteristics being processed by the machine learning classifier.

15. The computer usable program product of claim 12, wherein determining that a match is found between the first set of fluid characteristics and the second set of fluid characteristics includes determining that the first set of fluid characteristics matches the second set of fluid characteristics within a predetermined threshold value.

16. The computer usable program product of claim 12, wherein the first set of fluid characteristics includes color space characteristics of the first fluid and the second set of fluid characteristics of the second fluid includes color space characteristics of the second fluid.

17. The computer usable program product of claim 16, wherein the color space characteristics of the first fluid and the second fluid include at least one of a hue distribution and a saturation distribution of the first fluid and the second fluid.

18. The computer usable program product of claim 16, wherein the first set of fluid characteristics of the first fluid further includes a viscosity of the first fluid and the second set of fluid characteristics of the second fluid further includes a viscosity of the second fluid.

19. The computer usable program product of claim 18, further comprising:

program instructions to determine the viscosity of the first fluid based upon a Brownian motion pattern detected from the first series of optical images; and program instructions to determine the viscosity of the second fluid based upon a Brownian motion pattern detected from the second series of optical images.

20. A computer system comprising one or more processors, one or more computer-readable memories, and one or more computer-readable storage devices, and program instructions stored on at least one of the one or more storage devices for execution by at least one of the one or more processors via at least one of the one or more memories, the stored program instructions comprising:

program instructions to receive a first series of optical images of a first fluid;

program instructions to determine a first set of fluid characteristics of the first fluid from the first series of optical images, a fluid characteristic in the first set of fluid characteristics comprising color space characteristics of the first fluid;

program instructions to receive a second series of optical images of a second fluid;

program instructions to determine a second set of fluid characteristics of the second fluid from the second series of optical images, a fluid characteristic in the second set of fluid characteristics comprising color space characteristics of the second fluid;

program instructions to determine that a match is found between the first set of fluid characteristics and the second set of fluid characteristics; and program instructions to identify the second fluid based upon determining that the first set of fluid characteristics matches the second set of fluid characteristics.

* * * * *